(12) United States Patent
Shieh et al.

(10) Patent No.: US 10,086,015 B2
(45) Date of Patent: Oct. 2, 2018

(54) **USE OF IRON OXIDE NANOPARTICLE IN INHIBITING SPORE GERMINATION OF *CLOSTRIDIUM DIFFICILE***

(71) Applicant: Dar-Bin Shieh, Tainan (TW)

(72) Inventors: Dar-Bin Shieh, Tainan (TW); Pei-Jane Tsai, Taipei (TW); Wei-Ting Lee, Tainan (TW); Tsung-Ju Li, Tainan (TW); Chen-Sheng Yeh, Tainan (TW); Shang-Rung Wu, New Taipei (TW)

(*) Notice: Subject to any disclaimer, the term of this patent is extended or adjusted under 35 U.S.C. 154(b) by 0 days.

(21) Appl. No.: 15/326,655

(22) PCT Filed: Jul. 17, 2015

(86) PCT No.: PCT/CN2015/084303
§ 371 (c)(1),
(2) Date: Jan. 17, 2017

(87) PCT Pub. No.: WO2016/008444
PCT Pub. Date: Jan. 21, 2016

(65) Prior Publication Data
US 2017/0202879 A1    Jul. 20, 2017

Related U.S. Application Data

(60) Provisional application No. 62/025,497, filed on Jul. 17, 2014.

(51) Int. Cl.
*A61K 33/26* (2006.01)
*A61K 9/00* (2006.01)
*A61K 9/14* (2006.01)

(52) U.S. Cl.
CPC ............ *A61K 33/26* (2013.01); *A61K 9/0019* (2013.01); *A61K 9/14* (2013.01)

(58) Field of Classification Search
None
See application file for complete search history.

(56) References Cited

FOREIGN PATENT DOCUMENTS

WO    WO2010136792 A2 * 12/2010

OTHER PUBLICATIONS

Huang et al., "Size-control synthesis of structure deficient truncated octahedral Fe3-δO4 nanoparticles: high magnetization magnetites as effective hepatic contrast agents", 2011, 21, pp. 7472-7479.*
Ravikumar et al., "Antibacterial Activity of Metal Oxide Nanoparticles Against Ophthalmic Pathogens", Jul. 2011, vol. 3(5): pp. 122-127.*

* cited by examiner

*Primary Examiner* — Robert A Wax
*Assistant Examiner* — Randeep Singh

(57) ABSTRACT

Disclosed herein is a use of $Fe_{3-\delta}O_4$ nanoparticle in inhibiting the spore germination of *Clostridium difficile*. The $Fe_{3-\delta}O_4$ nanoparticle specifically targets the spores of *Clostridium difficile* spores by damaging and breaking the intact structure of the *Clostridium difficile* spores. Further, the $Fe_{3-\delta}O_4$ nanoparticle possesses superior sporicidal activity, as compared to other known bactericidal nanoparticles. Therefore, the $Fe_{3-\delta}O_4$ nanoparticle of the disclosure is useful as a bactericide or more specifically, a sporicide to treat *Clostridium difficile* infection for its superior sporicidal activity.

15 Claims, 18 Drawing Sheets

USE OF IRON OXIDE NANOPARTICLE IN INHIBITING SPORE GERMINATION OF *CLOSTRIDIUM DIFFICILE*

BACKGROUND OF THE INVENTION

1. Field of the Invention

The present disclosure relates to inhibition of *Clostridium difficile*. More particularly, the present disclosure relates to a novel use of $Fe_{3-\delta}O_4$ nanoparticle in inhibiting the spore germination of *Clostridium difficile*.

2. Description of Related Art

Spore formation enables bacteria to survive harsh environment and nutrition deprivation, including resisting ultraviolet radiation, desiccation, high temperature, extreme freezing and chemical disinfectants. The spores can reactivate itself to the vegetative state when the environment becomes favorable. Therefore, the spore-forming pathogens present a challenge to clinical disease management and prevention, e.g., infection of *Bacillus* and *Clostridium*. *Clostridium difficile*, a pathogen associated with healthcare—relevant infections, particularly, *C. difficile* infection (CDI), is one of the major causes for antibiotic treatment related diarrhea, pseudomembranous colitis, abdominal pain, fever and death. Once CDI is found, only a few antibiotics are available to contain the disease. Furthermore, both the failure rate of first-line antibiotics and the relapse rate are high. As a consequence, the attributable mortality rate is 6.9% at 30 days after diagnosis and 16.7% at 1 year.

The spores of *C. difficile* are the major cause of CDI. Compared to oxygen sensitive vegetative bacteria, *C. difficile* spores may sustain harsh environment (such as the hospital surfaces) for up to several months. It is known that the normal flora in gut can suppress the growth of *C. difficile* and therefore may suppress CDI. However, CDI usually occurs in patients that are subjected to long-term use of antibiotics, and it is often initiated by the spores acquired from healthcare workers. As the spores enter the human digestive tract, they germinate upon being exposed to taurocholate or their derivatives and then colonized in the colon. The virulence of *C. difficile* dependents on the expression of tcdA encoding toxin A, an enterotoxin, and tcdB encoding toxin B, a cytotoxin, respectively. Both would cause intestinal inflammation and the neutrophils infiltration in the infected foci.

In view of the increasing incidence of CDI, which is becoming a major cause of healthcare-associated infection in the world, how to efficiently control or treat CDI becomes an urgent issue. A number of different antibiotics have been used for the treatment of CDI, including Metronidazole, Vancomycin, and Fidaxomicin. Although those antibiotics usually can slow or stop the symptom associated with CDI, they may also lead to the development of antibiotics-resistant strain of *C. difficile*. Besides, appearance of spores that are resistant to chemical agents further deteriorates the CDI clinical management. Some newly designed cholate derivatives exhibit promising effect against CDI; however they are still under pre-clinical study. Sodium hypochlorite, a standard disinfectant, exhibits outstanding antimicrobial activity, yet it also possesses unfavorable effects including corrosive property and irritation to tissues.

Due to the non-satisfactory therapeutic efficacy of the known typical treatments, various novel approaches are now being developed and attempt to solve this healthcare distress. Among these approaches, nanoparticles have attracted significant interests for their antibacterial properties acting through different mechanisms, including the generation of reactive oxygen species, disruption of cell membrane, release of toxic ions, and/or thio group-binding capacity. The known nanoparticles with the antibacterial property include Ag, ZnO, $TiO_2$, and zero-valent iron nanoparticles. Nevertheless, most current anti-bacteria nanoparticles possess biocidal activity against vegetative cells, but not the sporicidal activity against spores.

In view of the foregoing, there exist a need in the related art to develop an effective and biocompatible spore control strategy so as to control the spore germination and to treat CDI.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, disclosure herein features a novel use of $Fe_{3-\delta}O_4$ nanoparticle in inhibiting the spore germination of *C. difficile*, wherein $\delta$ is a number between 0 and 0.3. Accordingly, the $Fe_{3-\delta}O_4$ nanoparticle can be used to manufacture of a medicament for treating CDI.

One aspect of the present disclosure is directed to a method of inhibiting the spore germination of *C. difficile* in vitro. The method comprises incubating an effective amount of a $Fe_{3-\delta}O_4$ nanoparticle with the spore of *C. difficile*, wherein $\delta$ is a number between 0 and 0.3.

According to some embodiments of the present disclosure, the nanoparticle has a shape of a truncated octahedron, in which each edge of the truncated octahedron has a length of about 5 to 25 nm. In one embodiment, the length of each edge is about 14 nm. In another embodiment, the length of each edge is about 22 nm.

According to some embodiments of the present disclosure, the effective amount of the nanoparticle is at least 5 µg/mL; and preferably between about 5 to 500 µg/mL.

The present disclosure are also directed to compositions and/or methods for treating a subject having or suspected of having CDI. Accordingly, the composition comprises an effective amount of the $Fe_{3-\delta}O_4$ nanoparticle described above, wherein $\delta$ is a number between 0 and 0.3; and a pharmaceutically acceptable carrier. The nanoparticle has a shape of a truncated octahedron. According to some embodiments of the present disclosure, each edge of the truncated octahedron has a length between about 5 to 25 nm. In one preferred embodiment of the present disclosure, the length of each edge is about 14 nm. In another specific embodiment, the length of each edge is about 22 nm.

The method comprises administering to the subject a therapeutically effective amount of the composition of the present disclosure to alleviate or ameliorate the symptom of CDI. According to some embodiments of the present disclosure, about 0.4 to 4 mg $Fe_{3-\delta}O_4$ nanoparticle/Kg body weight may be administered to the subject; preferably about 2-4 mg $Fe_{3-\delta}O_4$ nanoparticle/Kg is administered to the subject.

According to some embodiments of the present disclosure, the $Fe_{3-\delta}O_4$ nanoparticle may be administrated by a route that is any of oral, nasal, or parenteral administration. The parental administration may be any of intramuscular, intravenous, subcutaneous, or intraperitoneal injection.

Many of the attendant features and advantages of the present disclosure will become better understood with reference to the following detail description.

BRIEF DESCRIPTION OF THE DRAWINGS

The present description will be better understood from the following detailed description read in light of the accompanying drawings, where.

Figure 1A:
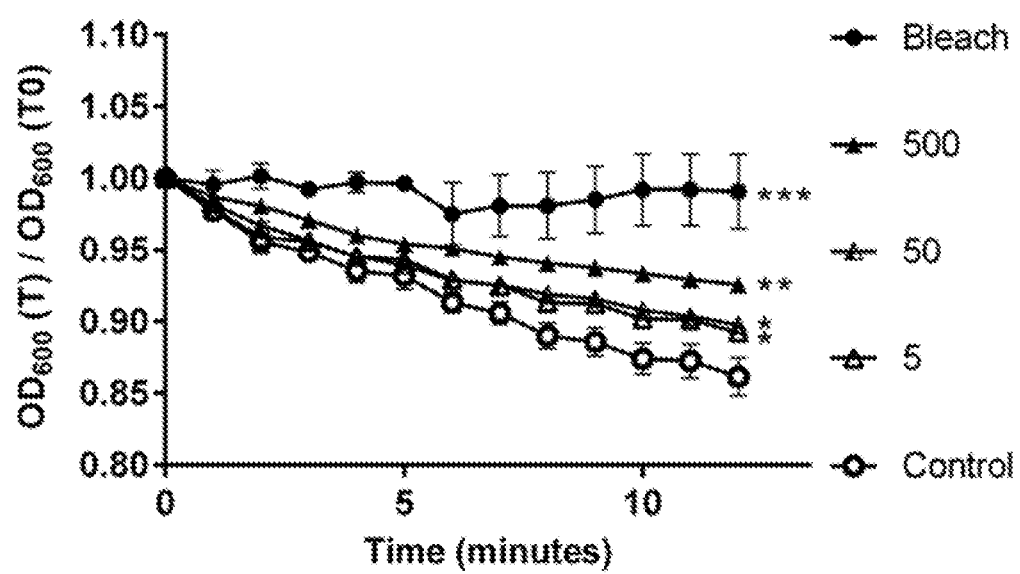
FIG. 1 are diagrams illustrating the kinetics of *C. difficile* spore germination, wherein the spores are respectively treated with (A) ZnO nanoparticle, (B) Ag nanoparticle, (C) $Fe_2O_3$ nanoparticle, (D) $Fe_3O_4$ nanoparticle, (E) non-oxidized iron core-gold shell nanoparticle (hereinafter designated as "Fe@Au nanoparticle"), and (F) $Fe_{3-\delta}O_4$ nanoparticle, according to Example 1.1 of the present disclosure.
Figure 1B:
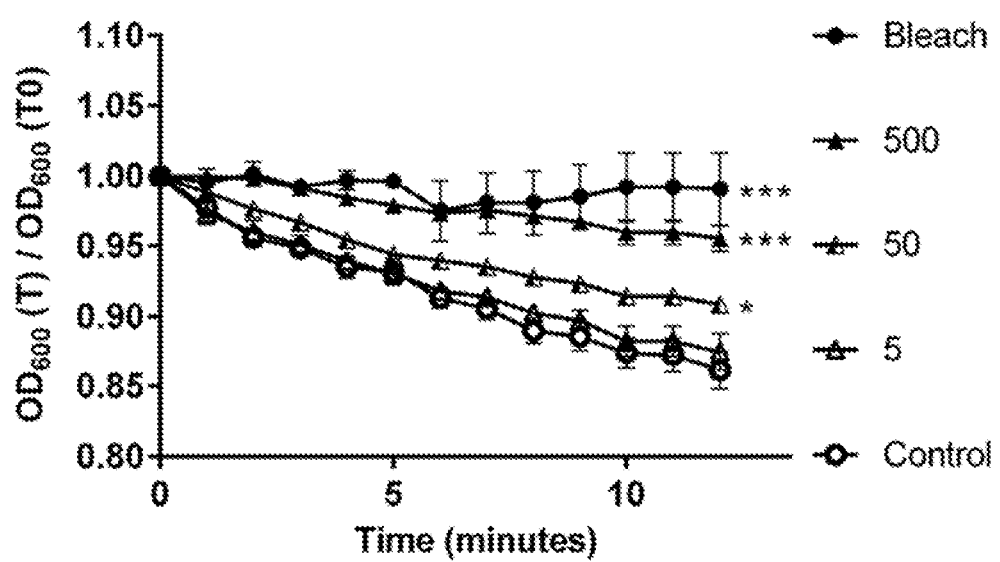
Figure 1C:
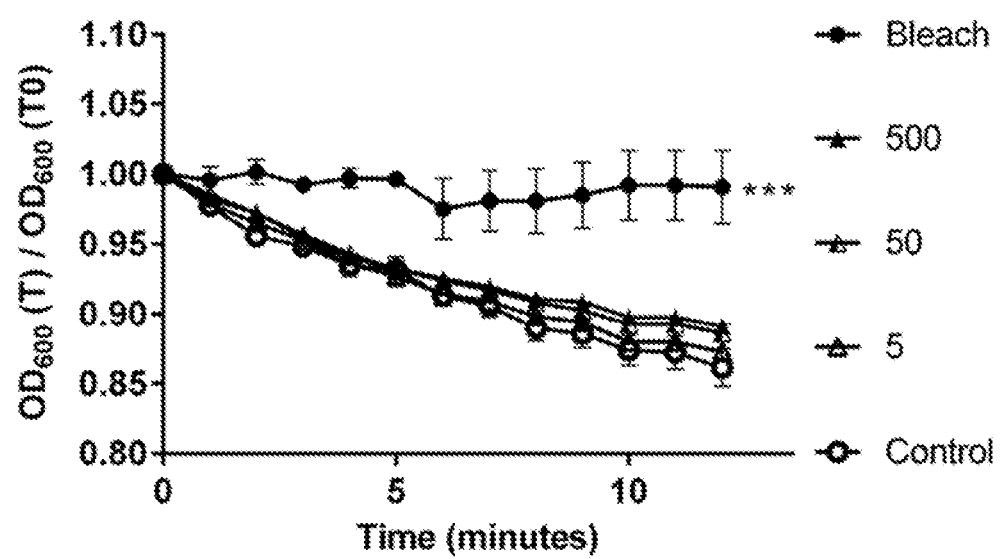
Figure 1D:
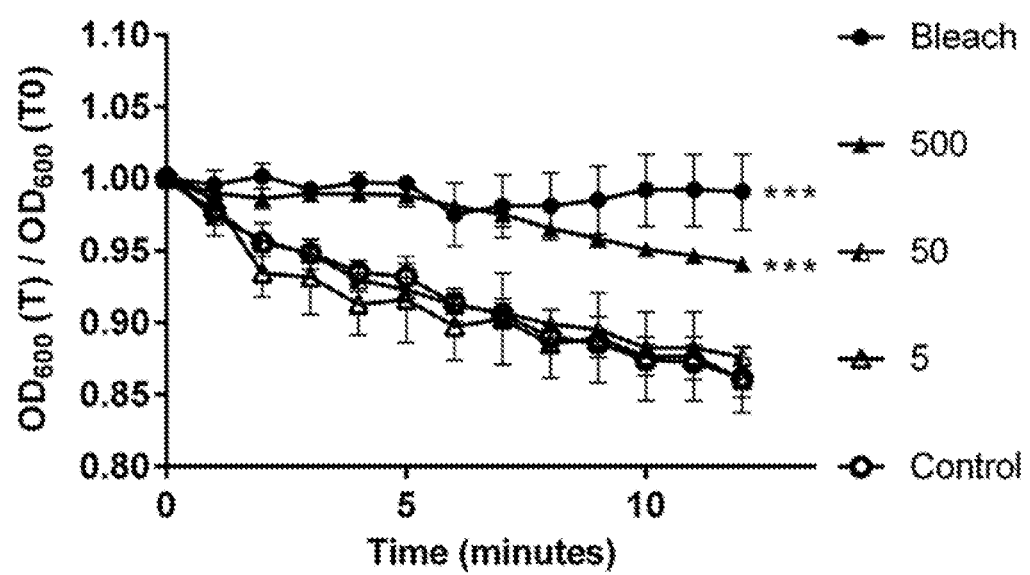
Figure 1E:
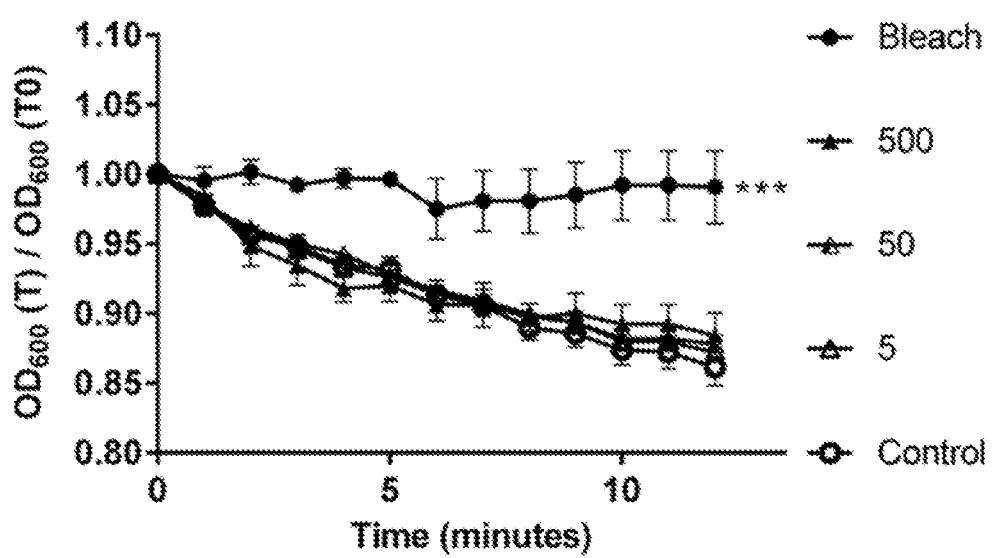
Figure 1F:
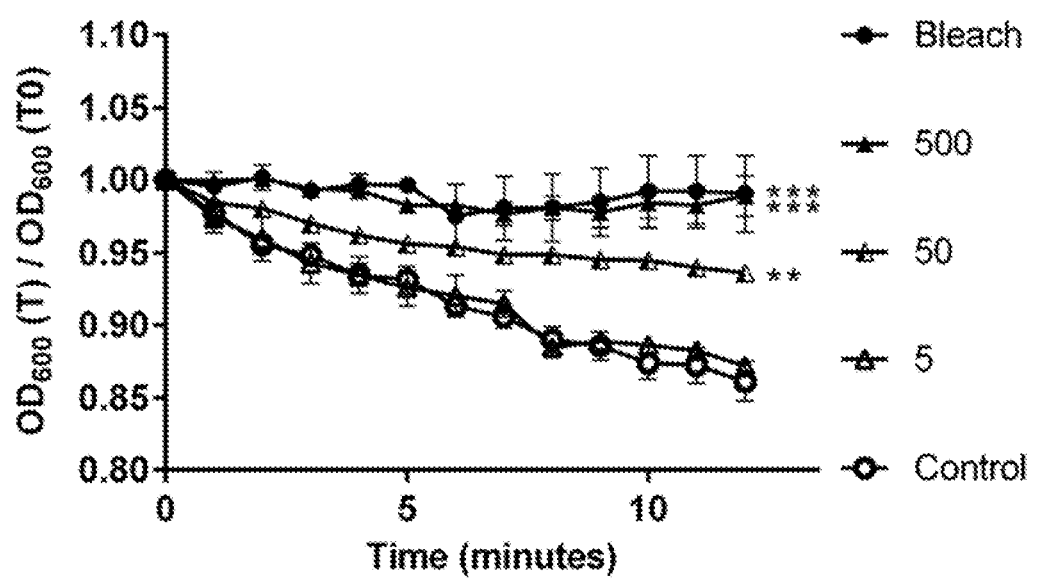

In accordance with common practice, the various described features/elements are not drawn to scale but instead are drawn to best illustrate specific features/elements relevant to the present invention.

DETAILED DESCRIPTION OF PREFERRED EMBODIMENTS

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attaching claims are approximations that can vary as desired. At the very least, each numerical parameter should at least be construed in light of the number of reported significant digits and by applying ordinary rounding techniques.

As used herein, the term "nonstoichiometric" used to describe a chemical compound with an elemental composition that cannot be represented by a ratio of well-defined natural number and therefore violate the law of definite proportions. That is, a nonstoichiometric compound does not contain exactly the same proportion of elements by mass.

As used herein, the term "treating" encompasses partially or completely preventing, ameliorating, mitigating and/or managing a symptom, a secondary disorder or a condition associated with CDI. The term "treating" as used herein refers to application or administration of the $Fe_{3-\delta}O_4$ nanoparticles to a subject, who has a symptom, a secondary disorder, or a condition associated with CDI, with the purpose to partially or completely alleviate, ameliorate, relieve, delay onset of, inhibit progression of, reduce severity of, and/or reduce incidence of one or more symptoms, secondary disorders or features of CDI. Symptoms, secondary disorders, and/or conditions associated with CDI include, but are not limited to, diarrhea, abdominal pain, fever, foul stool odor, pseudomembranous colitis and death. Treatment may be administered to a subject who exhibits only early signs of such symptoms, disorder, and/or condition for the purpose of decreasing the risk of developing the symptoms, secondary disorders, and/or conditions associated with CDI. Treatment is generally "effective" if one or more symptoms or clinical markers are reduced as that term is defined herein. Alternatively, a treatment is "effective" if the progression of a symptom, disorder or condition is reduced or halted.

The term "therapeutically effective amount" as used herein refers to the quantity of a component (such as the $Fe_{3-\delta}O_4$ nanoparticle of the present invention) which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. A therapeutically effective amount is also one in which any toxic or detrimental effects of the component or composition are outweighed by the therapeutically beneficial effects. Effective amount may be expressed, for example, in grams, milligrams or micrograms or as milligrams per kilogram of body weight (mg/kg). Alternatively, the effective amount can be expressed in the concentration of the active component in the pharmaceutical composition, such as molar concentration, mass concentration, volume concentration, molality, mole fraction, mass fraction and mixing ratio. Specifically, the term "therapeutically effective amount" used in connection with the $Fe_{3-\delta}O_4$ nanoparticle described herein refers to the quantity of the $Fe_{3-\delta}O_4$ nanoparticle, which is sufficient to alleviate or ameliorate the symptom of CDI in the subject.

The term "subject" refers to a mammal including the human species that is treatable with the method of the present disclosure. The term "subject" is intended to refer to both the male and female gender unless one gender is specifically indicated.

The practices of this invention are hereinafter described in detail with respect to a novel use of $Fe_{3-\delta}O_4$ nanoparticle in inhibiting the spore germination of C. difficile, wherein $\delta$ is a number between 0 and 0.3. Accordingly, the $Fe_{3-\delta}O_4$ nanoparticle can be used to treat CDI.

One aspect of the present disclosure is directed to a method of inhibiting the spore germination of C. difficile in vitro. The method comprises the step of incubating an effective amount of $Fe_{3-\delta}O_4$ nanoparticle with the spore of C. difficile, so as to suppress the germination of the C. difficile spore. Compared to $Fe_3O_4$ (i.e., magnetite) or $\gamma$-$Fe_2O_3$ (i.e., maghemite), the $Fe_{3-\delta}O_4$ of the present disclosure is partially oxidized and nonstoichiometric, wherein $\delta$ is a non-integer number between 0 and 0.3.

The $Fe_{3-\delta}O_4$ of the present disclosure may be prepared in according to any previously known method. For example, by the method exemplified in Examples of the present disclosure. Typically, the method comprises steps of:

(1) dissolving iron acetylacetonate in oleic acid and trioctylamine to form a mixture solution;

(2) refluxing the mixture solution of step (1) under an inert environment (e.g., vacuum or in the presence of $N_2$ or Ar) for about 30 minutes;

(3) collecting the precipitates of step (2) with a magnet;

(4) washing the collected precipitates of step (3) with toluene;

(5) collecting the washed precipitates of step (4) with the magnet;

(6) adding the collected precipitates of step (5) into a poly(styrene-alt-maleic acid)-containing chloroform solution to form the $Fe_{3-\delta}O_4$ nanoparticles and (7) collecting the $Fe_{3-\delta}O_4$ nanoparticles of step (6) with the magnet.

The $Fe_{3-\delta}O_4$ nanoparticle prepared in accordance with the method described above may have a shape of a truncated octahedron, with the length of each edge of the truncated octahedron ranges from about 5 to 25 nm. For example, each edge of the truncated octahedron may be 5, 6, 7, 8, 9, 10, 11, 12, 13, 14, 15, 16, 17, 18, 19, 20, 21, 22, 23, 24, or 25 nm in length. In one example, the $Fe_{3-\delta}O_4$ nanoparticle has an edge length about 14 nm. In another example, the $Fe_{3-\delta}O_4$ nanoparticle has an edge length about 22 nm.

According to some embodiments of the present disclosure, the $Fe_{3-\delta}O_4$ nanoparticles respectively having the edge length of 14 nm and 22 nm are capable of suppressing the germination of C. difficile spore. In one example, the C. difficile spore is derived from CCUG 37780 strain. In another example, the C. difficile spore is derived from CCUG 19126 strain. In still another example, the C. difficile spore is derived from ATCC BAA-1805 strain.

According to other embodiments, the $Fe_{3-\delta}O_4$ nanoparticle of the present disclosure exhibits sporicidal activity without interfering with the growth of vegetative normal flora.

In other embodiments of the present disclosure, the $Fe_{3-\delta}O_4$ nanoparticle exhibits superior inhibitory activity against C. difficile spore over that of ZnO nanoparticle, Ag nanoparticle, $Fe_2O_3$ nanoparticle, $Fe_3O_4$ nanoparticle, or Fe@Au nanoparticle.

According to one embodiment of the present disclosure, the $Fe_{3-\delta}O_4$ nanoparticle is capable of directly binding to the spore surface of C. difficile, and disrupting the intact structure of the spore and thereby leading to the leakage of the intracellular protein from the spore.

According to some embodiments of the present disclosure, to suppress germination of the C. difficile spores, the present nanoparticles are administered to the intended site or target, in which the C. difficile spores exist, in a concentration of at least 5 μg/mL, preferably from about 5 to 500 μg/mL. An exemplary effective amount of the nanoparticles is 50 μg/mL, while another exemplary effective amount of the nanoparticle is 500 μg/m L.

Another aspect of the present disclosure is directed to a method of treating a subject having or suspected of having CDI. The method comprises the step of, administering to the subject a therapeutically effective amount of $Fe_{3-\delta}O_4$ nanoparticle of the present disclosure to alleviate or ameliorate the symptom of CDI, wherein the $Fe_{3-\delta}O_4$ nanoparticle is partially oxidized and δ is a non-integer number between 0 and 0.3.

According to some embodiments of the present disclosure, the treatment efficacy of $Fe_{3-\delta}O_4$ nanoparticle is not limited to CDI caused by specific *C. difficile* spore, such as spores from CCUG 37780, CCUG 19126, or BAA-1805 strain; but rather to CDI caused by the spores of any *C. difficile* strains.

The $Fe_{3-\delta}O_4$ nanoparticles suitable for administering to the subject respectively has a shape of a truncated octahedron with an edge length between about 5 to 25 nm, such as 5, 6, 7, 8, 9, 10, 11, 12, 13, 14, 15, 16, 17, 18, 19, 20, 21, 22, 23, 24, or 25 nm. In one embodiment of the present disclosure, the truncated octahedron has an edge that is about 14 nm in length; while in another embodiment, the edge length of the truncated octahedron is about 22 nm.

According to some embodiments of the present disclosure, the $Fe_{3-\delta}O_4$ nanoparticle is administered to the subject by a route that is any of oral, nasal, or parenteral administration, in an amount between about 0.4 to 4 mg/Kg; that is, the amount is any of 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 mg/Kg. Preferably, the amount is about 2-4 mg/Kg.

The $Fe_{3-\delta}O_4$ nanoparticle of the present disclosure can be administered during and/or after CDI. In one embodiment, the $Fe_{3-\delta}O_4$ nanoparticle is administered during CDI, and 2 mg/Kg of $Fe_{3-\delta}O_4$ nanoparticle is sufficient to alleviate or ameliorate the symptom of CDI. In another embodiment, the $Fe_{3-\delta}O_4$ nanoparticle is administered after CDI, and both 2 mg/Kg and 4 mg/Kg $Fe_{3-\delta}O_4$ nanoparticle exhibit the sporicidal efficacy against CDI.

In some embodiments, the $Fe_{3-\delta}O_4$ nanoparticle is administered to the subject parenterally, which includes, but is not limited to, intramuscular, intravenous, subcutaneous, and intraperitoneal injection. In other embodiments, the nanoparticle is treated through oral administration.

The present disclosure provides a solution to solve the clinical healthcare distress associated with CDI. The following examples illustrate the use of $Fe_{3-\delta}O_4$ nanoparticle in the inhibition of the germination of *C. difficile* spore and/or the treatment of CDI. In preferred embodiments of the present disclosure, $Fe_{3-\delta}O_4$ nanoparticle could attenuate colitis induced by *C. difficile* spore. The examples are illustrative only, and do not limit the scope of the present invention.

EXAMPLES

Materials and Methods
Bacterial Incubation and Spore Purification

*C. difficile* CCUG37780 and CCUG19126 were purchased from the Culture Collections of the University of Goteborg (Goteborg, Sweden), and ATCC BAA1805 was purchased from American Type Culture Collection (Manassas, Va.). All strains were incubated in supplemented brain heart infusion medium (BHIS; 237500, BD Difco, Franklin Lakes, N.J.), with 0.5% yeast extract (212750, BD Difco) and 0.1% L-cysteine (7048046, Amresco, Solon, HO), at 37° C. under anaerobic conditions. The spores were prepared and purified in accordance with procedures described in previous study with slight modification ("Bile Salts and Glycine as Cogerminants for *Clostridium difficile* Spores." *J Bacteriol* 2008, 190: 2505-2512). Briefly, *C. difficile* in BHIS medium was diluted to 0.2 value of optic density 600 nm ($OD_{600}$) by adding therein the fresh BHIS medium. 900 μL of diluted bacterial suspension were added to 6-well dish with BHIS agar, and then the dish was incubated at 37° C. in an anaerobic jar (O-HP011A, Thermo Oxoid, Oxoid Ltd., Basingstoke, England) for 4 days. The cells were then collected from the 6-well dish with 1 mL ice-cold sterile Milli-Q (MQ) water and then placed at 4° C. overnight. After 5 times washes with ice-cold sterile water, bacteria were resuspended with 3 mL ice-cold sterile MQ water. The suspension was speaded on top of the 10 mL 50% (wt/vol) sucrose solution (409704, J.T. Baker Chemical Co., Phillipsburg, Pa.) in a centrifugal tube, and then centrifuged at 3,500 g for 20 minutes to separate spore from vegetative cells. The purified spores in the bottom of the centrifuge tube were washed 5 times with ice-cold sterile water to remove sucrose. The purified spores were stored at 4° C. until use.

Spore Germination 2 to 10 mM taurocholate was used in the present study to explore the spore germination response in strain CCUG 37780 of *C. difficile*. Stain CCUG 37780 lacks tcdA and tcdB gene and is considered as a relatively safe strain. The inhibitory activity of the nanoparticles on spore germination was tested using CCUG 37780 strain. *C. difficile* spores treated with 10 mM taurocholate exhibited the most prominent germination curve, as compared to those observed at other concentrations (p<0.0001, Tukey's Multiple Comparison test). Therefore, *C. difficile* spores pre-treated with 10 mM taurocholate were used in the following studies.

Nanoparticles Preparation

The $Fe_{3-\delta}O_4$ nanoparticles were prepared by thermal decomposition. Briefly, 1.42 g of iron acetylacetonate (517003, Sigma-Aldrich, St. Louis, Mo.) was mixed with 0.57 mL of oleic acid (27726, Sigma-Aldrich) and 20 mL of trioctylamine (T81000, Sigma-Aldrich). The solution was refluxed at 325° C. under the Ar environment for 30 minutes. After the solution cooled down to room temperature, the precipitate was collected with a magnet and washed three times with toluene. The $Fe_{3-\delta}O_4$ nanoparticles were collected with a magnet and transferred to the chloroform solutions (UN1888, Merck, Whitehouse Station, N.J.) containing 0.4 mg/mL poly(styrene-alt-maleic acid) (662631, Sigma-Aldrich) and let stand for 2 hours. The $Fe_{3-\delta}O_4$ nanoparticles were collected and washed 3 times with MQ water.

The Fe@Au nanoparticles were prepared by the following steps. 2.4 mL of $FeSO_4$ (0.5 M, 31236, Riedel-de Haën, Seelze, Germany) including 6 g cetyltrimethylammonium bromide (CTAB, H6269, Sigma-Aldrich), 5 g 1-butanol (33065, Sigma-Aldrich), and 15 g octane (296988, Sigma-Aldrich) were mixed with 2.4 mL of 1.0 M $NaBH_4$ in MQ water (71320, Sigma-Aldrich) for 5 minutes to form the iron nanoparticles solution. 1.8 mL of 0.44 M $HAuCl_4$ in MQ water (16961-25-4, Alfa Aesar, Ward Hill, Mass.) and 1.8 mL of 1.6 M $NaBH_4$ in MQ water were added into the iron nanoparticles solution and stirred for another 30 minutes. The Fe@Au nanoparticles were washed with the 99.9% ethanol (800605, J.T. Baker Chemical Co.) with a magnet.

ZnO nanoparticles were produced by chemical bath deposition system. 0.1 M zinc nitrate hexahydrate (263-00335, Wako, Osaka, Japan) and 0.1 M hexamethylenetetramine (081-00332, Wako) were blended together with a Si(100) substrate (Wafer Works Corporation, Taiwan) at 95° C. for 8 hours. After the reaction, the ZnO nanoparticles were washed with distilled water for 5 times.

The silver nanoparticles were synthesized in according to the following steps. Briefly, 3.4 mM of silver nitrate (s6506, Sigma-Aldrich) and 0.46 mM of Sodium citrate tribasic dihydrate (s4641, Sigma-Aldrich) were mixed by stirring at room temperature. The 8.8 mM of sodium borohydride was then added into the mixture, and the stirring was continued for 10 min at room temperature. The synthesized silver nanoparticles were stored in 99.9% ethanol.

The 6 nm $Fe_3O_4$ nanoparticles were purchased from Taiwan Advanced Nanotech (TANBead® USPIO-101).

Spore Germination Test Via Optic Density 600 nm Detection

Before the germination took place, the spore suspension was first incubated at 60° C. for 30 minutes in order to eliminate vegetative cells. The heat-treated spores were then moved to ice before use. The *C. difficile* spores with a concentration of $OD_{600}$ 0.5 were co-incubated with various nanoparticles and/or different concentration (5 to 500 µg/mL) in BHIS in a 96-well plate for 20 minutes. The spores treated with 3% bleach (197-02206, Wako) in the study were used as the positive control and spores in BHIS only as the negative control. After the particle co-incubation, 10 mM taurocholate (T4009, Sigma) was added to initiate the spore germination. The $OD_{600}$ of treated spores was determined kinetically by spectrophotometer (Ser. No. 16/039,400, TECAN, Grodig, Austria) at room temperature until 12 minutes, with a time interval of 1 minute. The spore germination time course was plotted against ODs respectively measured at different time points.

Germination Kinetic Assay

The purified and heated spores were incubated in BHIS with or without $Fe_{3-\delta}O_4$ (50 µg/mL) in a 96-well dish for 20 minutes and then treated with 2, 5, 10, 20, 40, or 50 mM taurocholate. The 3% bleach in the study was used as the positive control to inhibit germination. Once the taurocholate was added to the aliquots, $OD_{600}$ was measured.

The Spore Binding Assay

*C. difficile* BAA 1805 spores with a concentration of $OD_{600}$ 0.5 were co-incubated with $Fe_{3-\delta}O_4$ nanoparticles (500 µg/mL) in BHIS in a 96-well plate for 20 minutes. The spores without the addition of $Fe_{3-\delta}O_4$ nanoparticles were the controls. All samples were placed under a magnet for 5 minutes and then all supernatants were removed. The magnet-attracted parts and supernatant were washed with 1×PBS for 3 times, respectively. All samples were re-dissolved in distilled deionized water. The spores and nanoparticles were then imaged using a transmission electron microscope (TEM, JEM-1400, JEOL, Japan).

Protein Leakage Assay

The spores with a concentration of $OD_{600}$ 0.5 were co-incubated with $Fe_{3-\delta}O_4$ nanoparticles (500 µg/mL) in MQ water in a 96-well plate for 20 minutes. The samples were then centrifuged at 3,500 g for 10 minutes. The supernatant was removed and the pellet was re-suspended and sonicated. The bacterial lysate of respective groups was collected by centrifugation (8000 g, 4° C., 10 minutes) so as to measure the residual proteins inside the spore. The collected protein samples were subjected to 15% SDS-PAGE and silver staining with the stain kit (17-1150-01, Amersham Biosciences, Sppsala, Sweden) to visualize the relative amount of bacterial spore proteins.

In Vivo *C. difficile* Infection (CDI)

Animals were housed in a specific pathogen-free barrier facility, and all experimental procedures involving animals complied with relevant procedures approved by the Institutional Animal Care and Use Committe (IACUC) of National Cheng Kung University. Each mouse weighed about 25 g at the beginning of the test.

To directly monitor the colonic inflammation, a NF-κB-dependent reporter mouse model containing the luciferase transgene under the transcriptional control of NF-κB (NF-κB-RE-luciferase) was infected by the *C. difficile* spore. Before feeding the mice with spores, an antibiotic cocktail (0.4 mg/mL kanamycin, 0.035 mg/mL gentamicin, and 0.057 mg/mL colistin) was added to their drinking water for 48 hours, and fresh cocktail was replaced every 24 hours for 2 days. The mice were gavaged with 200 µL proton pump inhibitor (PPI, 2 mg/mL) every 12 hours for 2 days before *C. difficile* spore infection (CDI).

The mice were respectively infected with spores from strains of *C. difficiles*, i.e., CCUG 19126 and BAA-1805. In the group of CCUG 19126 infection, $2\times10^5$ CFU of *C. difficile* spore CCUG 19126 were co-incubated with or without 500 µg/mL $Fe_{3-\delta}O_4$ for 20 minutes before mice were gavaged with 100 µL distilled water (about 2 mg/Kg body weight). During the time when spores and $Fe_{3-\delta}O_4$ nanoparticles were co-incubated, all mice were gavaged with 50 µL PPI (2 mg/mL) and intraperitoneal injected with clindamycin (4 mg/kg). The antibiotic cocktail water was replaced to normal water after the CDI.

In the group of BAA-1805 infection, the mice were fed with *C. difficile* spore BAA-1805 ($2\times10^5$ CFU) after they were gavaged with a 50 µL PPI (2 mg/mL) and intraperitoneally injected with clindamycin (4 mg/kg). After 24 hours, the mice were respectively gavaged 100 µL of 0, 500 and 1000 µg/mL $Fe_{3-\delta}O_4$ nanoparticles (about 0, 2 and 4 mg/Kg body weight) every 24 hours for 2 day.

All mice were monitored for CDI symptoms including diarrhea, weight loss, hunched posture, and death. 72 hours after the infection, luciferin (Xenogen, PerkinElmer, Waltham, Mass.), a luciferase substrate, at the dose of 150 mg/kg was injected intraperitoneally to induce the NF-κB activation-mediated luminescence. Mice were anesthetized with isoflurane/oxygen and images were collected for 5 min by IVIS Spectrum Imaging system (Xenogen). Data was analyzed by LivingImage® software (Xenogen) and luciferase activity was presented in photons/sec/cm2/steradian (p/s/cm2/sr). After the IVIS images were obtained, RNA was extracted from cola by TRI Reagent (T9424, Sigma). The levels of inflammatory genes expression were measured via real-time PCR (StepOnePlus, Applied Biosystems). To estimate the rate of CDI, the stool were collected and the DNA in stool were purified with the DNA extraction kit (11814770001, Roche). The tcdB gene in the mouse stool were detected via PCR.

Histopathological Analysis

Histopathological analysis was performed to evaluate mucosal damage and inflammation induced by the CDI. Resected colon tissues were fixed in 4% formaldehyde buffered with PBS and then embedded in paraffin. Deparaffinized 6 µm-thick sections were stained with hematoxylin and eosin for histological analysis, which was performed with the aid of a microscope. Neutrophil number were randomly counted with 10 fields, for spores alone group, and spores treated with $Fe_{3-\delta}O_4$ group.

Statistical Analysis

Statistical analysis was performed by GraphPad Prism version 5.01. All experiments in this study were triplicated, and data was reported as means±standard error of the mean (SEM) from three independent experiments. The one-way ANOVA conjugated with Tukey's Multiple Comparison test was used in spore germination curve analysis, and Student's t-test was used in the other CFU inhibition test. P<0.05, 0.01, 0.001 were taken as the level of significance using in both the statistical methods.

Example 1 Sporicidal Activity of $Fe_{3-\delta}O_4$ Nanoparticle

The use of $Fe_{3-\delta}O_4$ nanoparticle in inhibiting the spore germination of *C. difficile* was evaluated in the following examples.

1.1 Sporicidal Activity of $Fe_{3-\delta}O_4$ Nanoparticle Against Spores of *C. difficile*

Various nanoparticles are known to possess excellent bactericidal properties without affecting surrounding tissue. However, the interaction between nanoparticles and bacterial spore germination has not yet been fully investigated. To explore the interaction between spore germination and bactericidal nanoparticles, ZnO nanoparticles, Ag nanoparticles, $Fe_2O_3$ nanoparticles, $Fe_3O_4$ nanoparticles, Fe@Au, and $Fe_{3-\delta}O_4$ nanoparticles were tested in the present study. The 20-mins bleach inactivated spores were used as positive control, according to the literature report. After co-incubating bacterial spores with various concentrations of nanoparticles ranging from 5, 50, to 500 μg/mL for 20 mins, the spores were then stimulated by the addition of 10 mM taurocholate to induce spore germination.

The result illustrated in FIG. 1 indicated that well-known bactericidal nanoparticles including ZnO (FIG. 1A), Ag (FIG. 1B), and $Fe_3O_4$ nanoparticle (FIG. 1D), respectively had limited spore germination inhibition activity. Furthermore, the strain CCUG 37780 of *C. difficile* did not react to fully oxidized $Fe_2O_3$ nanoparticle (FIG. 1C), nor to Fe@Au nanoparticle (FIG. 1E), in the present study. Although 5 μg/mL $Fe_{3-\delta}O_4$ nanoparticle had marginal effect on spore germination, yet 50 and 500 μg/mL $Fe_{3-\delta}O_4$ nanoparticle exhibited outstanding inhibitory effects towards spore germination (FIG. 1F). Particularly, at the concentration of 500 μg/mL, the inhibitory effect of $Fe_{3-\delta}O_4$ nanoparticle on spore germination was not statistically different from that of the bleach positive control (p>0.5, Tukey's Multiple Comparison test, FIG. 1F).

These data indicated that, compared with other known bactericidal nanoparticles, the $Fe_{3-\delta}O_4$ nanoparticle of the present disclosure does possess superior sporicidal activity, and both 50 and 500 μg/mL $Fe_{3-\delta}O_4$ nanoparticle treatments could effectively prevent the spores from forming active vegetative cells.

1.2 Sporicidal Activity of $Fe_{3-\delta}O_4$ Nanoparticle Having Various Sizes

Figure 2:
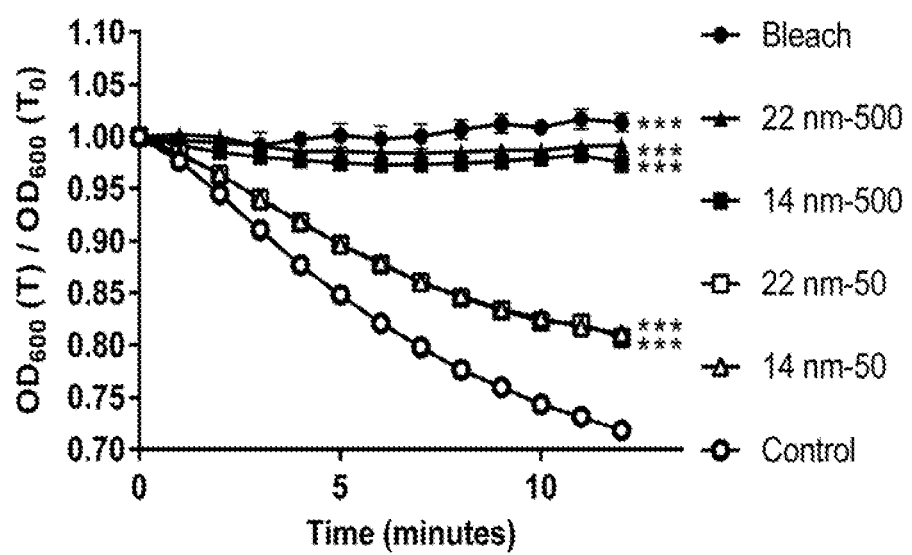
FIG. 2 is a diagram illustrating the kinetics of *C. difficile* spore germination, wherein the spores are respectively treated with 500 μg/mL of 22 nm-$Fe_{3-\delta}O_4$ (▲), 500 μg/mL of 14 nm-$Fe_{3-\delta}O_4$ (■), 50 μg/mL of 22 nm-$Fe_{3-\delta}O_4$ (□), 50 μg/mL of 14 nm-$Fe_{3-\delta}O_4$ (Δ), and 3% bleach (●), according to Example 1.2 of the present disclosure.
Figure 3A:
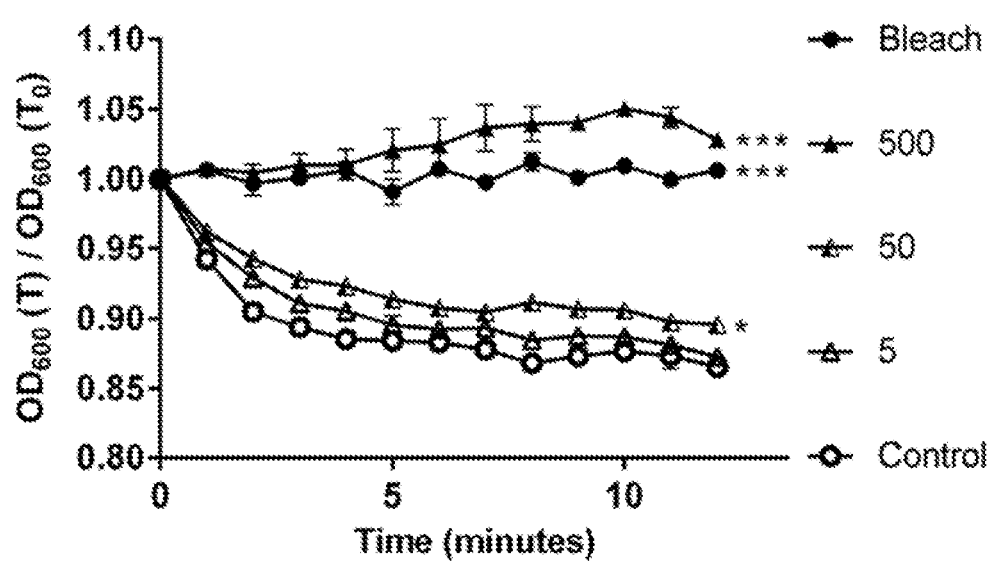
FIG. 3 are diagrams illustrating the kinetics of *C. difficile* spore germination, wherein the spores of strain CCUG 19126 (A) and strain ATCC BAA-1805 (B) were respectively treated with 500 μg/mL of $Fe_{3-\delta}O_4$ (▲), 50 μg/mL of $Fe_{3-\delta}O_4$ (◢), 5 μg/mL of $Fe_{3-\delta}O_4$ (Δ), and 3% bleach (●), according to Example 1.3 of the present disclosure.
Figure 3B:
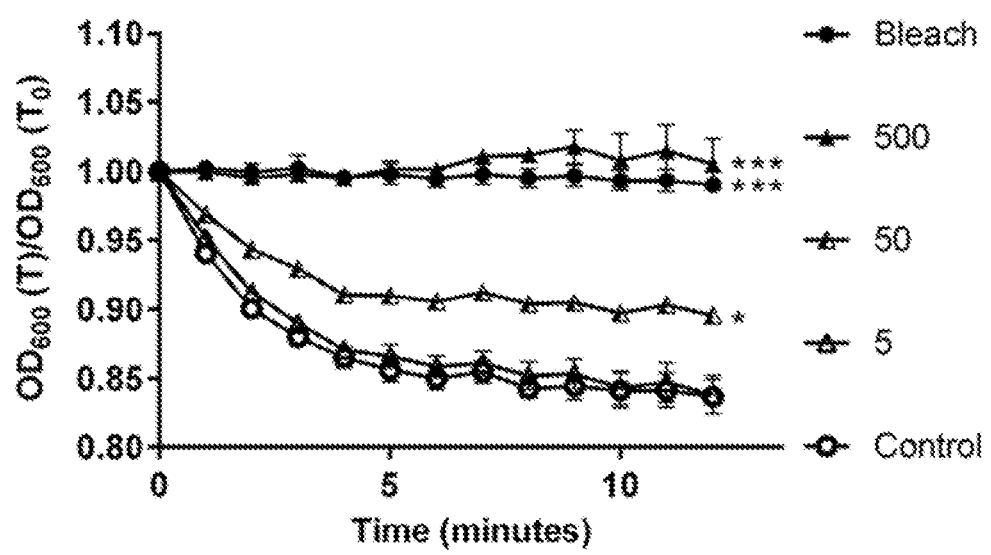
Figure 4:
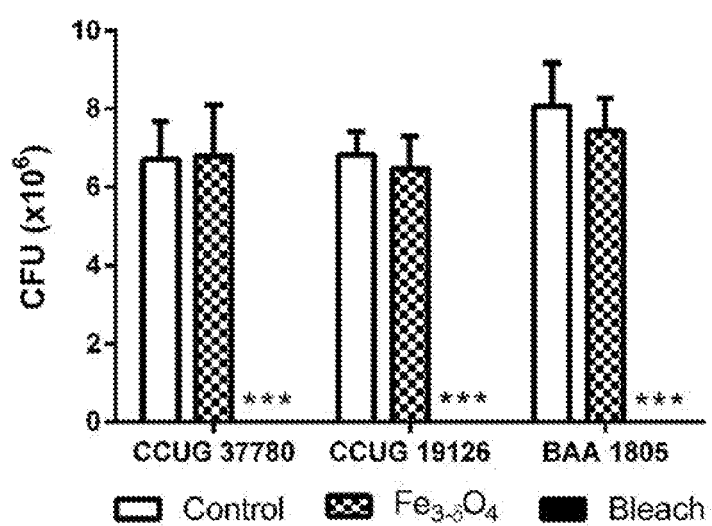
FIG. 4 is a histogram illustrating the viability of *C. difficile* vegetative cells respectively treated with control, $Fe_{3-\delta}O_4$ nanoparticle, and bleach, according to Example 1.4 of the present disclosure.
Figure 5:
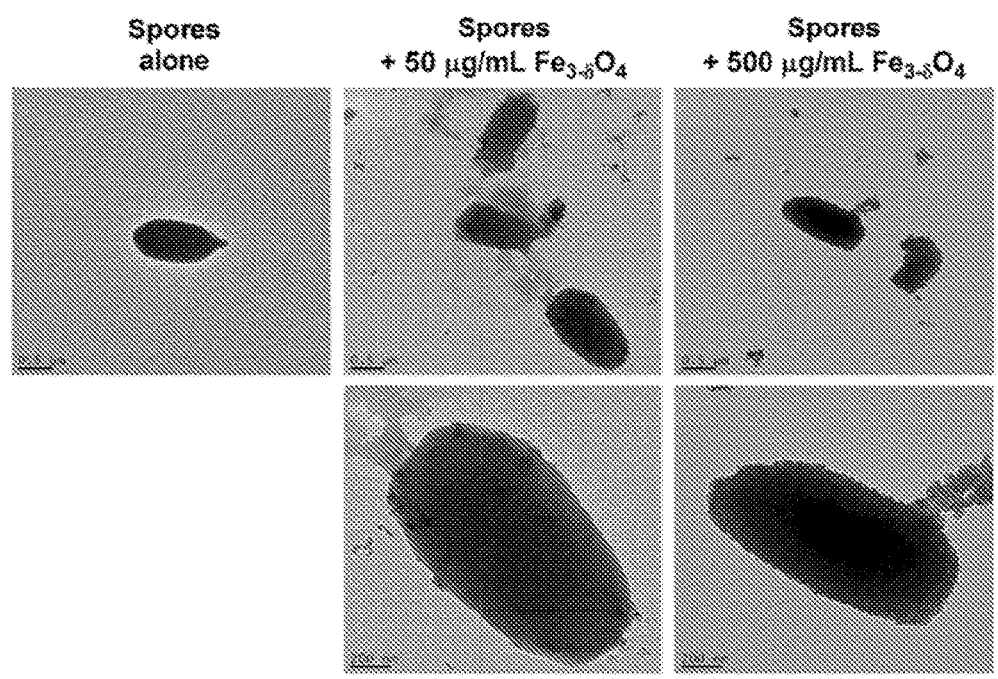
FIG. 5 are TEM images of *C. difficile* spores respectively treated with mock control (spores alone), 50 μg/mL $Fe_{3-\delta}O_4$, and 500 μg/mL $Fe_{3-\delta}O_4$; the photographs were taken with the magnification of 10,000× (upper panel) and 30,000× (lower panel), respectively, according to Example 2 of the present disclosure.
Figure 6:
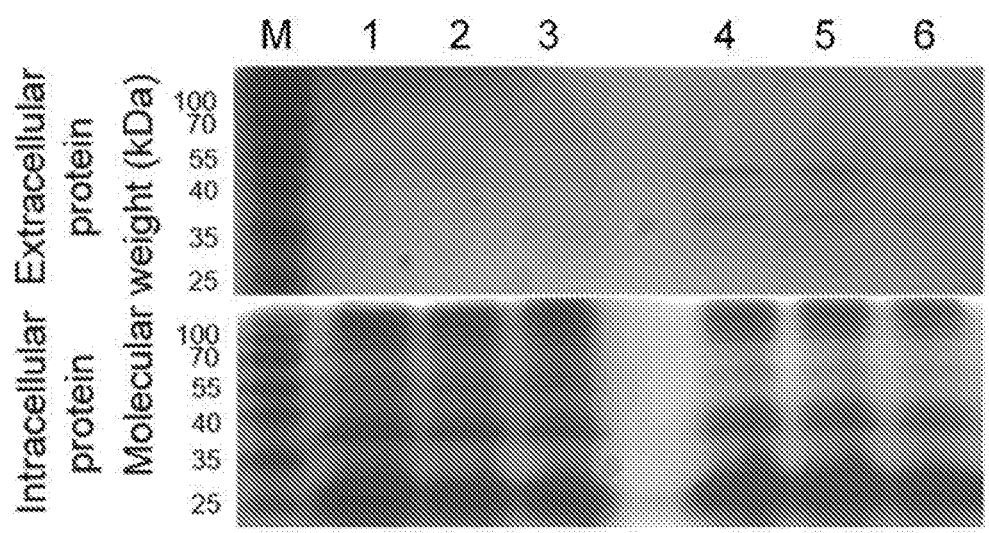
FIG. 6 are SDS-polyacrylamide gel electrophoresis (SDS-PAGE) analysis of extracellular protein (upper panel) and intracellular protein (lower panel) of *C. difficile* spores with (lane 4-6) or without (lane 1-3) $Fe_{3-\delta}O_4$ nanoparticle treatment, according to Example 2 of the present disclosure.

Since the $Fe_{3-\delta}O_4$ nanoparticles may be synthesized as truncated octahedrons with edge length ranging from 5 to 25 nm, the size effect of $Fe_{3-\delta}O_4$ nanoparticle might have on spore germination was further investigated. Accordingly, two $Fe_{3-\delta}O_4$ nanoparticles respectively having different edge length (i.e., 14 nm vs. 22 nm) were used to treat spores of CCUG 37780 strain. The data of FIG. 2 demonstrates that there was no significant differences between these two nanoparticles in terms of inhibiting spore germination ($p=0.5195$ for 500 μg/mL concentration and $p>0.99$ for 50 μg/mL, Tukey's Multiple Comparison test). Therefore, it is the concentration, rather than the size, of $Fe_{3-\delta}O_4$ nanoparticle, that is responsible for the inhibitory activity of *C. difficile* spore germination.

1.3 Sporicidal Activity of $Fe_{3-\delta}O_4$ Nanoparticle Against Spores of Different Stains of *C. difficile*

In this example, the inhibitory activity of $Fe_{3-\delta}O_4$ on spores of tcdA and tcdB positive strains of *C. difficile*, i.e., CCUG 19126 and ATCC BAA-1805 were investigated. Accordingly, CCUG 19126 and ATCC BAA-1805 strains were exposed to various concentrations of $Fe_{3-\delta}O_4$ nanoparticle (i.e., 5, 50, and 500 μg/mL) for 20 minutes prior to 10 mM taurocholate treatment. Results are depicted in FIG. 3.

As FIG. 3 illustrated, $Fe_{3-\delta}O_4$ nanoparticle exhibited similar effects on both CCUG 19126 (FIG. 3A) and ATCC BAA-1805 (FIG. 3B) strains at the concentration of 500 μg/mL, whereas CCUG 19126 was relatively more resistant to $Fe_{3-\delta}O_4$ nanoparticle at the concentration lower than 50 μg/mL (FIG. 3A).

The data suggested that the inhibitory activity of the $Fe_{3-\delta}O_4$ nanoparticle on spore germination is not specific to any particular strains of *C. difficile*. In other words, the $Fe_{3-\delta}O_4$ nanoparticle is effective to spores of all strains of *C. difficile*.

1.4 Bactericidal Activity of $Fe_{3-\delta}O_4$ Nanoparticle Against Vegetative Cells of *C. difficile*

Despite the superior spore germination inhibition activity, the bactericidal property of $Fe_{3-\delta}O_4$ nanoparticle against vegetative cells was further investigated among different strains of *C. difficile*. The vegetative cells were first treated with 500 μg/mL $Fe_{3-\delta}O_4$ nanoparticle for 20 minutes, and then spread on the BHIS agar plates for further CFU counting. As depicted in FIG. 4, the $Fe_{3-\delta}O_4$ nanoparticle treated cells exhibited similar growth behavior that was comparable to the negative control groups; whereas the growth of 3% bleach treated cells was nearly eliminated completely.

Taken together, the inhibitory activity of the $Fe_{3-\delta}O_4$ nanoparticle of the present disclosure on spore germination was common among different strains of *C. difficile*, including CCUG 37780, CCUG 19126, and ATCC BAA-1805; however, it was ineffective toward vegetative cells of *C. difficile*.

Example 2 Characterization of $Fe_{3-\delta}O_4$ Nanoparticle Against Spores of *C. difficile*

In order to clarify the interaction between $Fe_{3-\delta}O_4$ and spores, the $Fe_{3-\delta}O_4$ treated spores are examined under the transmission electron microscopy (TEM). As evidenced from the TEM images, $Fe_{3-\delta}O_4$ nanoparticles started to bind to spores at 50 μg/mL $Fe_{3-\delta}O_4$; and with the concentration of $Fe_{3-\delta}O_4$ nanoparticles increased to 500 μg/mL, the spores were completely covered by $Fe_{3-\delta}O_4$ nanoparticles, which existed in excess amount (FIG. 5). Thus, $Fe_{3-\delta}O_4$ nanoparticles bind to *C. difficile* spores directly in a dose dependent manner.

To further clarify whether the direct binding of $Fe_{3-\delta}O_4$ might cause damage and eventually disrupt the intact structure of spores, the $Fe_{3-\delta}O_4$ nanoparticle-treated spores (or without $Fe_{3-\delta}O_4$ nanoparticles treated) was further analyzed for any protein leaking therefrom using SDS-PAGE. Results are illustrated in FIG. 6.

Compared to the untreated spores, two major protein bands were observed in the supernatant of $Fe_{3-\delta}O_4$ treated spores (FIG. 6, lanes 1 to 3 vs. lanes 4 to 6). The results suggested that once $Fe_{3-\delta}O_4$ nanoparticle bound to spores, it may have caused certain damages to the structure of the spores, and thus led to proteins being leaked into the supernatant.

The data in sum indicated that the $Fe_{3-\delta}O_4$ nanoparticle of the present disclosure could directly bind to the spores of *C. difficile*, and subsequently cause damage thereof.

Example 3 Use of $Fe_{3-\delta}O_4$ Nanoparticle in the Treatment of *C. difficile* Infection (CDI)

In this example, the in vivo efficacy of $Fe_{3-\delta}O_4$ nanoparticles on CDI was investigated using a previously developed NF-κB-dependent reporter mouse model in accordance with steps described in "Material and Methods" section. In example 3.1, the mice were infected with *C. difficile* spore CCUG 19126, and the therapeutic efficacy of the $Fe_{3-\delta}O_4$ nanoparticles is illustrated in FIG. 7. In example 3.2, the mice were infected with *C. difficile* spore BAA-1805, and the result is illustrated in FIG. 8.

3.1 CCUG 19126 Infection

Figure 7A:
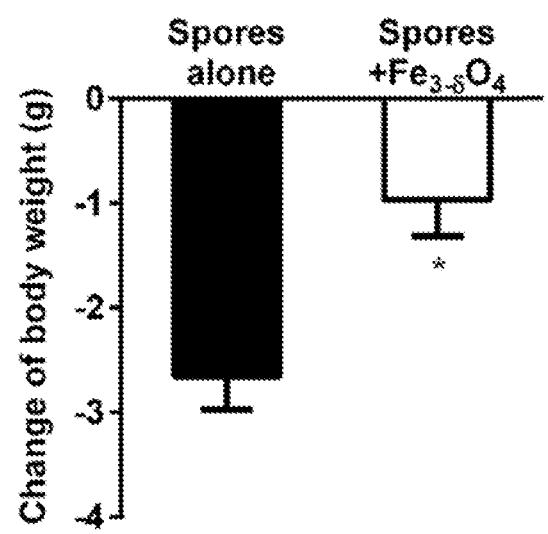
FIG. 7A is a histogram illustrating the mean weight-loss of spore-induced CDI mice with (the white bar) or without (the black bar) $Fe_{3-\delta}O_4$ nanoparticle treatment, according to Example 3.1 of the present disclosure.
Figure 7B:
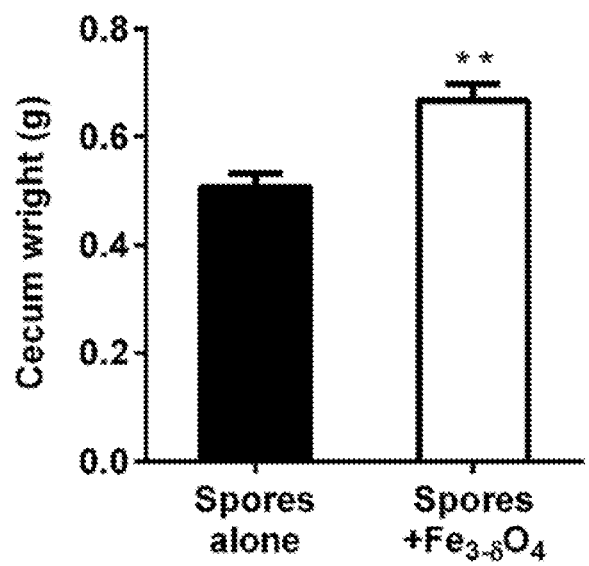
FIG. 7B is a histogram illustrating the cecum weight of spore-induced CDI mice with (the white bar) or without (the black bar) $Fe_{3-\delta}O_4$ nanoparticle treatment, according to Example 3.1 of the present disclosure.
Figure 7C:
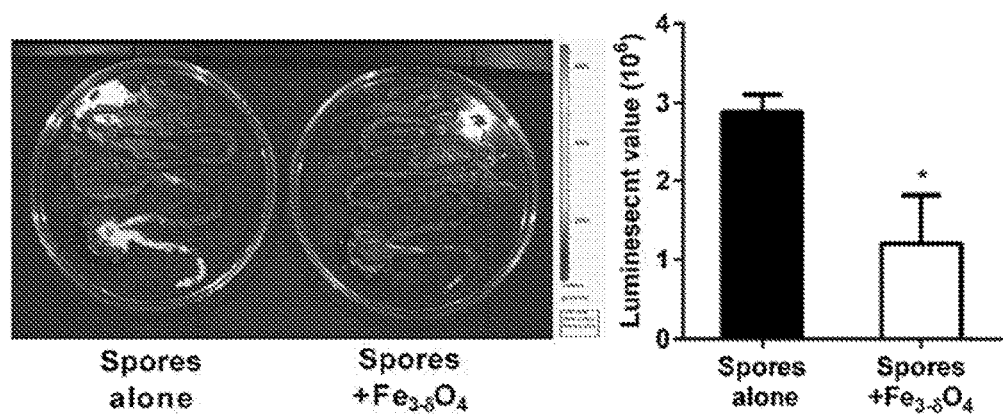
FIG. 7C illustrates the inflammation status of the cecums respectively isolated from spore-induced CDI mice with or without $Fe_{3-\delta}O_4$ nanoparticle treatment; the images are detected by In Vivo Imaging Systems (IVIS) (the left panel) and data are analyzed and presented as histogram (the right panel), according to Example 3.1 of the present disclosure.
Figure 7D:
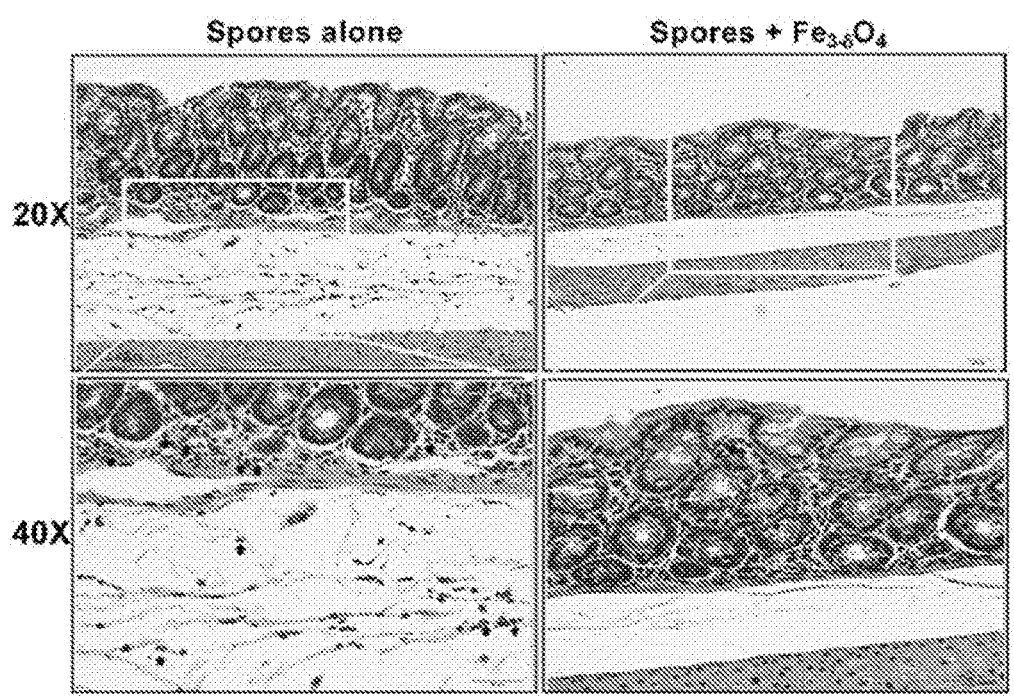
FIG. 7D are photographs depicting the histopathological images of colon tissues respectively isolated from spore-induced CDI mice with (the right panel) or without (the left panel) $Fe_{3-\delta}O_4$ nanoparticle treatment; the photographs are taken respectively under the microscope with the magnification of 20× or 40×, according to Example 3.1 of the present disclosure.
Figure 7E:
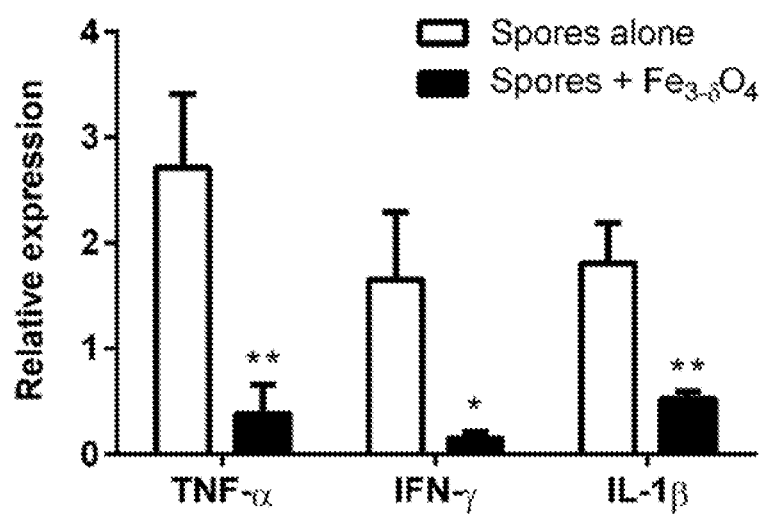
FIG. 7E is a histogram illustrating RNA expression of indicated inflammatory genes; RNA is respectively extracted from the colon of spore-induced CDI mice with (the black bar) or without (the white bar) $Fe_{3-\delta}O_4$ nanoparticle treatment, according to Example 3.1 of the present disclosure.
Figure 8:
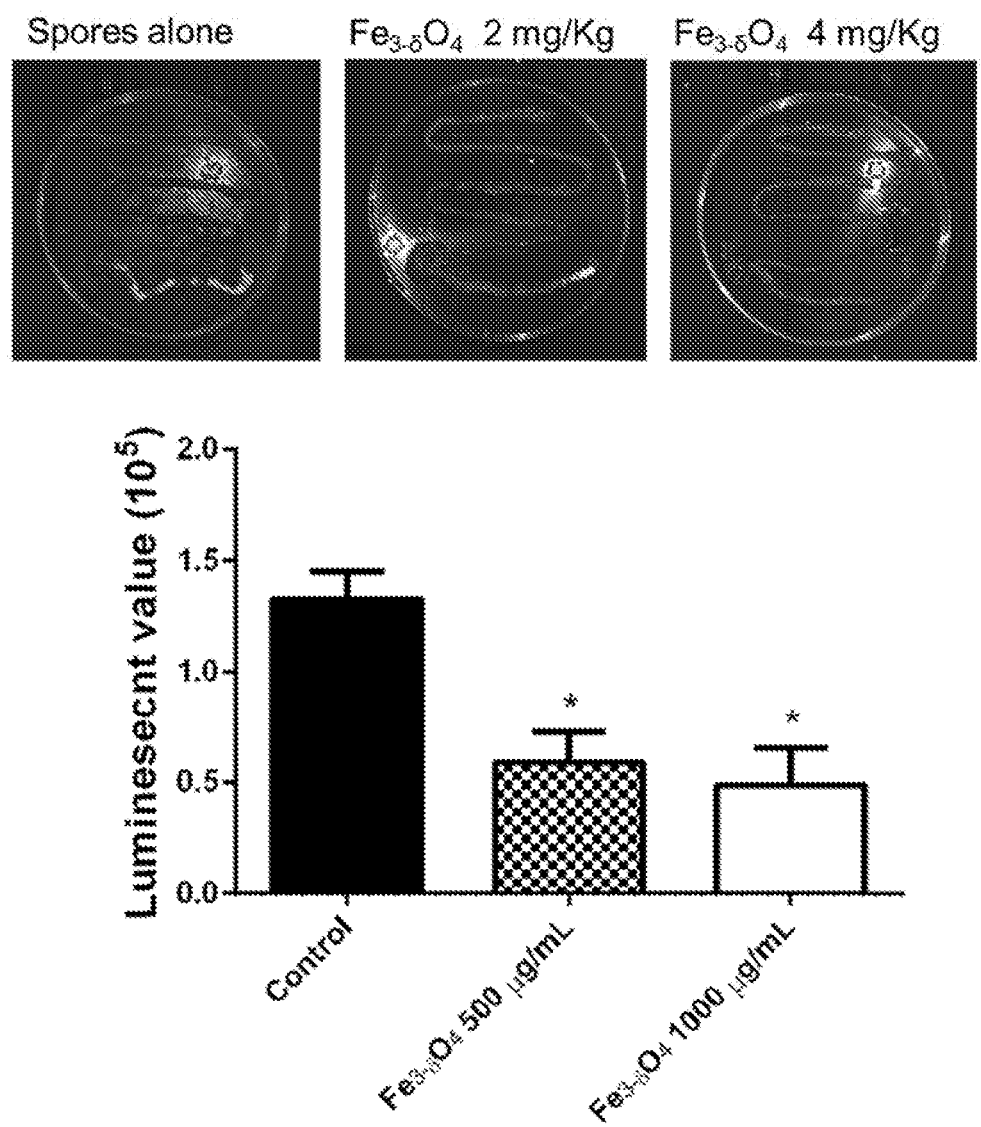
FIG. 8 illustrates the inflammation status of the cecums respectively isolated from spore-induced CDI mice treated with 0, 2, or 4 mg $Fe_{3-\delta}O_4$ nanoparticle/Kg body weight; the images are detected by IVIS (the upper panel) and data are analyzed and presented as histogram (the lower panel), according to Example 3.2 of the present disclosure.

Animals with CDI infection exhibited significant weight loss, which was greatly attenuated by the treatment of $Fe_{3-\delta}O_4$ nanoparticles (2 mg/Kg body weight, p=0.0119, Student's t-test) (FIG. 7A). The attenuation on weight loss was confirmed by the measurement of cecum weight, in which cecum of $Fe_{3-\delta}O_4$ treated group was heavier and healthier than that of the control group (p=0.0024, Student's t-test, FIG. 7B), and exhibited minor inflammation (p=0.0406, Student's t-test, FIG. 7C). The histopathological images also confirmed that the neutrophil infiltration was reduced in the $Fe_{3-\delta}O_4$ treated group (FIG. 7D), as compare to that of the control group. Further, at the molecular level, quantitative real-time PCR confirmed that in the $Fe_{3-\delta}O_4$ treated group, the expression of inflammatory genes, including TNF-$\alpha$, IFN-$\gamma$, and IL-1$\beta$, diminished significantly, as compared with those of the control group (p=0.0088 for TNF-$\alpha$, p=0.0276 for IFN-$\gamma$, and p=0.0097 for IL-1$\beta$, Student's t-test, compared to spores alone groups, FIG. 7E). Moreover, the CDI rate of $Fe_{3-\delta}O_4$ treated spores group (33%) was lower than that of the control group (66%) (data not shown).

Taken together, the results demonstrated that treatment of 2 mg/Kg $Fe_{3-\delta}O_4$ may reduce the level of inflammation caused by the spore CCUG 19126 of *C. difficile*.

3.2 BAA-1805 Infection

The therapeutic efficacy of $Fe_{3-\delta}O_4$ on another *C. difficile* spore-BAA-1805 was investigated in this example. To further mimic the clinical situation, the mice were infected with the spore BAA-1805 for 24 hours, followed by the treatment of 0, 2, or 4 mg/Kg $Fe_{3-\delta}O_4$ nanoparticle.

According to the data of FIG. 8, the colon inflammatory signal was stronger in the control group (i.e., spores alone), than in the $Fe_{3-\delta}O_4$ nanoparticles treatment groups (p<0.05). Both dosage of $Fe_{3-\delta}O_4$ nanoparticles (i.e., 2 and 4 mg/Kg) could efficiently suppress the inflammation induced by the spore BAA-1805 of *C. difficile*.

Accordingly, the present $Fe_{3-\delta}O_4$ nanoparticle may be administered during or after CDI, and both treatment time points can efficiently suppress the symptom associated with CDI.

Taken as a whole, the $Fe_{3-\delta}O_4$ nanoparticle is capable of inhibiting the spore germination of *C. difficile*. Compared to other known nanoparticles with bactericidal activity, the $Fe_{3-\delta}O_4$ nanoparticles exhibit superior sporicidal activity. Significantly, the inhibitory effect of $Fe_{3-\delta}O_4$ nanoparticles is not limited to the spores of certain *C. difficile* strains, but is effective to all strains. Further, low dose (e.g., 5 µg/mL for in vitro applications, and 2 mg/Kg for in vivo applications) $Fe_{3-\delta}O_4$ nanoparticles is sufficient enough to suppress spore germination of *C. difficile*, while the growth of vegetative normal flora remains unaffected, as well as in treating CDI infection of a subject.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of inhibiting in vitro spore germination of *Clostridium difficile*, comprising incubating a spore of *Clostridium difficile* with an effective amount of a $Fe_{3-\delta}O_4$ nanoparticle, wherein $\delta$ is a number between 0 and 0.3.

2. The method of claim 1, wherein the nanoparticle has a shape of a truncated octahedron.

3. The method of claim 2, wherein each edge of the truncated octahedron has a length of about 5 to 25 nm.

4. The method of claim 3, wherein the length is about 14 nm.

5. The method of claim 3, wherein the length is about 22 nm.

6. The method of claim 1, wherein the effective amount of the nanoparticle is about 5 to 500 µg/mL.

7. A method of treating a subject having or suspected of having *Clostridium difficile* infection comprising administering to the subject a therapeutically effective amount of a $Fe_{3-\delta}O_4$ nanoparticle to alleviate or ameliorate the symptom of *Clostridium difficile* infection, wherein $\delta$ is a number between 0 and 0.3, and the $Fe_{3-\delta}O_4$ nanoparticle inhibits the spore germination of *Clostridium difficile*.

8. The method of claim 7, wherein the nanoparticle has a shape of a truncated octahedron.

9. The method of claim 8, wherein each edge of the truncated octahedron has a length of about 5 to 25 nm.

10. The method of claim 9, wherein the length is about 14 nm.

11. The method of claim 9, wherein the length is about 22 nm.

12. The method of claim 7, wherein the therapeutically effective amount of the nanoparticle is about 0.4 to 4 mg/Kg.

13. The method of claim 12, wherein the therapeutically effective amount of the nanoparticle is about 2 to 4 mg/Kg.

14. The method of claim 7, wherein the nanoparticle is administrated by a route selected from the group consisting of oral, nasal, or parenteral administration.

15. The method of claim 14, wherein the parental administration is any of intramuscular, intravenous, subcutaneous, or intraperitoneal injection.

* * * * *